United States Patent
Mollat et al.

(10) Patent No.: US 8,158,417 B2
(45) Date of Patent: Apr. 17, 2012

(54) RECOMBINANT CELL LINES FOR THE STABLE AND HIGH-LEVEL PRODUCTION OF BIOLOGICALLY ACTIVE DKK1 PROTEIN

(75) Inventors: Patrick Mollat, Cergy (FR); Corinne Gillard, Gressy en (FR)

(73) Assignee: Galapagos SAS, Romainville (FR)

( * ) Notice: Subject to any disclaimer, the term of this patent is extended or adjusted under 35 U.S.C. 154(b) by 1031 days.

(21) Appl. No.: 12/090,793

(22) PCT Filed: Oct. 20, 2006

(86) PCT No.: PCT/EP2006/067620
§ 371 (c)(1),
(2), (4) Date: Apr. 18, 2008

(87) PCT Pub. No.: WO2007/045690
PCT Pub. Date: Apr. 26, 2007

(65) Prior Publication Data
US 2008/0248526 A1    Oct. 9, 2008

(30) Foreign Application Priority Data
Oct. 21, 2005  (FR) .................................... 05 10748

(51) Int. Cl.
*C12N 5/00*        (2006.01)

(52) U.S. Cl. ....................................................... 435/325
(58) Field of Classification Search .................. 435/325
See application file for complete search history.

(56) References Cited

FOREIGN PATENT DOCUMENTS
WO   WO 2004/085620 A2   10/2004
WO   WO 2005/095448 A2   10/2005

OTHER PUBLICATIONS

Valery E. Krupnik et al., Functional and Structrual Diversit of the Human Dickkopf Gene Family, Gene, Elsevier, Amsterdam, NL, vol. 238, No. 2., Oct. 1, 1999, pp. 301-313, XP-002140768.
Sheri L. Holmen et al., "Wnt-Independent Activation of β-catenin Mediated by a Dkk1-Fz5 Fusion Protein", Biochemical and Biophysical Research Communications, Jan. 2005, pp. 533-539.
FreeStyle 293 Expression System:, Invitrogen Life Technologies, Aug. 30, 2002, XP002389086, pp. 9-12.
International Search Report dated Feb. 9, 2007 (Four (4) pages).
Form PCT/ISA/220 and Form PCT/ISA/237 dated Feb. 9, 2007 (Seven (7) pages).

*Primary Examiner* — Maryam Monshipouri
(74) *Attorney, Agent, or Firm* — Crowell & Moring LLP

(57) ABSTRACT

This invention relates to the use of specific recombinant cell lines in order to produce biologically active DKK1 protein in a stable and high-level manner. The invention also relates to these recombinant cell lines, as well as a method for stable and high-level production of biologically active DKK1 protein, implementing such recombinant cell lines.

1 Claim, 5 Drawing Sheets

D)

1 2 3 4 5

E)

MW A B C D E

A)

B)

A)

B)

C)

Figure 1:
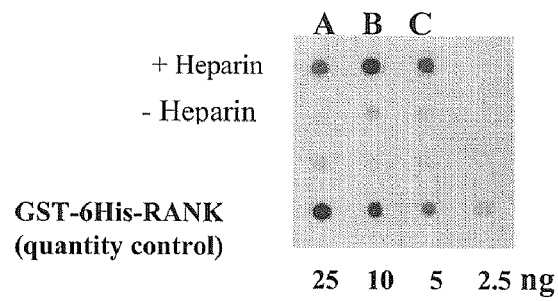
Figure 1:
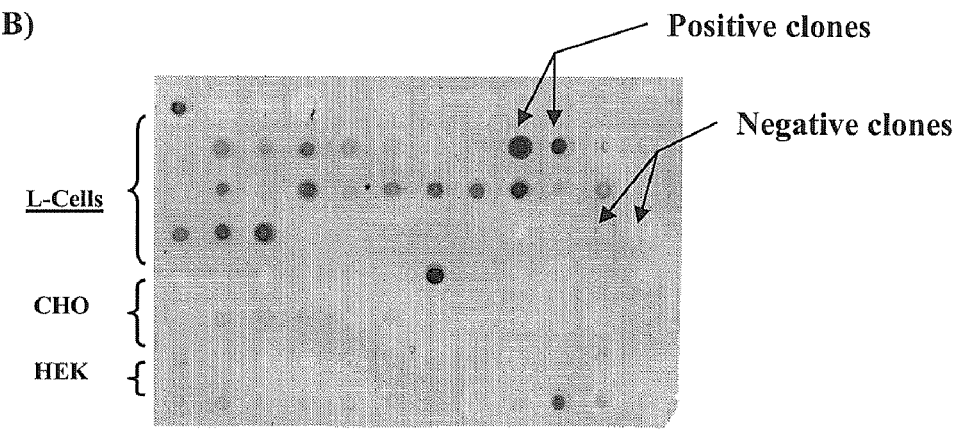
Figure 1:
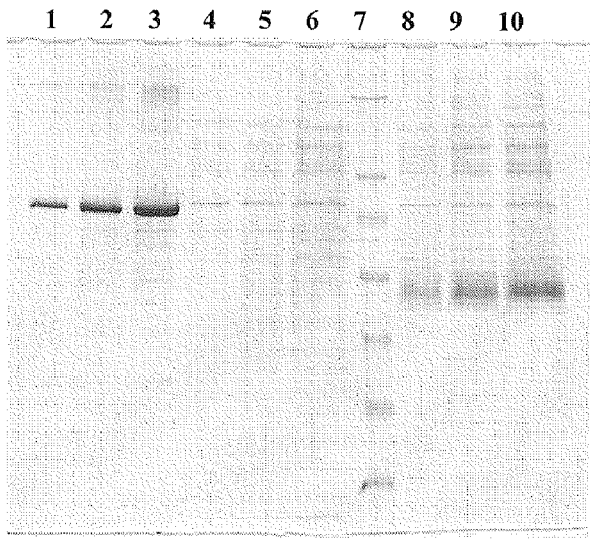
Figure 1:
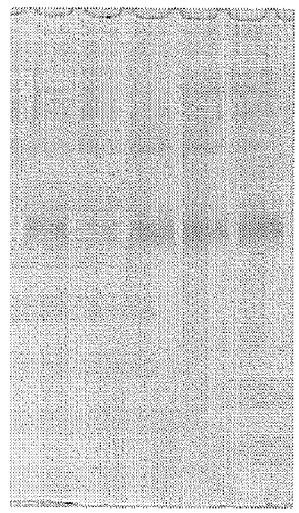
Figure 1:
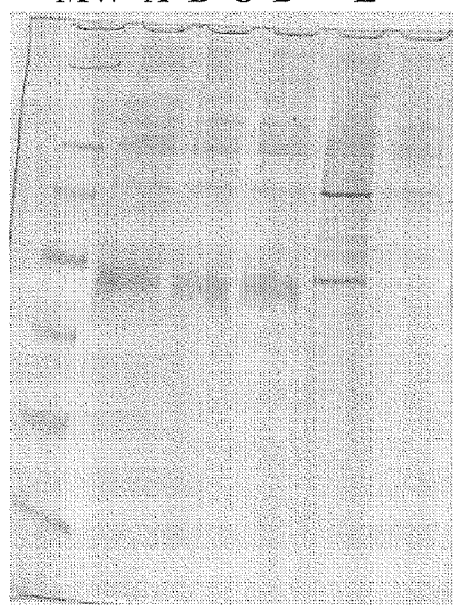

RECOMBINANT CELL LINES FOR THE STABLE AND HIGH-LEVEL PRODUCTION OF BIOLOGICALLY ACTIVE DKK1 PROTEIN

This application is a 371 of PCT/EP2006/067620 filed Oct. 20, 2006, which claims foreign priority to French application 0510748 filed Oct. 21, 2005.

This invention relates to the field of the stable and high-level production of biologically active proteins for purposes as diverse as, for example, research, industrial applications (in particular, for the agro-food or pharmaceutical industry) and medical applications (for therapy or diagnostics).

More specifically, this invention relates to the use of specific recombinant cell lines in order to produce biologically active DKK1 protein stably and at a high level. The invention also relates to these recombinant cell lines, as well as a method for stable and high level production of biologically active DKK1 protein, implementing such recombinant cell lines.

The Wnt signalling pathway plays a key role in embryonic development, differentiation of various cell types, and oncogenesis (Peifer and Polakis, 2000). Dickkopf proteins (DKK) are secreted Wnt inhibitors (see the international patent application WO 00/12708 published on Sep. 3, 2000, under the heading PRO1316). The DKK-1 protein (WO 99/22000 published on Jun. 5, 1999) was identified as an inducer of head formation in Xenopus by inhibiting the Wnt signalling (Glinka et al, 1998). It has also been shown that DKK-1 was involved in limb development (Grotewold et al, 1999) and inhibited the Wnt-induced morphological transformation (Fedi et al, 1999). To this day, four DKK proteins have been identified in mammals: DKK-1, DKK-2, DKK-3 and DKK-4 (Krupnik et al, 1999).

DKK proteins are potential targets of choice in the screening for dysfunctions of the Wnt pathway and the development of suitable diagnostic and therapeutic means. In this way, these proteins, and in particular the DKK-1 protein, are of interest to many scientific teams throughout the world. However, research and development studies conducted by these teams require, in order to be successful, large amounts of biologically active protein.

It is precisely to respond to this need that the Inventors have sought effective means and methods to produce large amounts of biologically active DKK protein, in particular DKK-1. And the means and methods proposed in this context of the present invention make it possible for the first time to fulfil this need satisfactorily, in particular in terms of (i) simplicity and implementation time, (ii) cost, and (iii) efficacy.

By reflecting on the means for solving the aforementioned technical problem, the Inventors discovered that it was possible to produce a biologically active protein of interest, in particular a DKK protein such as DKK-1, by using recombinant cells derived from a line normally provided on the market for conducting transient transfection experiments. In addition, the Inventors were able to note that the production of proteins by these cells presented the advantage of being simple, stable over time and at a high level.

Thus, a first aspect of this invention relates to the use of a recombinant cell line derived from the FreeStyle™ 293-F mammalian cell line (sold by Invitrogen) for the stable and high-level production of biologically active DKK1 protein, preferably of murine origin.

By "recombinant cell line derived from the FreeStyle™ 293-F mammal cell line", it is referred here to a cell line obtained from the FreeStyle™ 293-F line, by introducing into it, by conventional molecular biology techniques, an exogenous nucleic acid sequence encoding the protein of interest to be produced. By "exogenous nucleic acid sequence", it is referred here to a sequence that is not naturally present in FreeStyle™ 293-F cells. This sequence can be natural, synthetic or recombinant. It can correspond to a native or modified sequence, in particular by adding and/or suppressing and/or substituting one or more bases. The exogenous sequence can be carried by a vector (or plasmid) contained in the cells, or be integrated in the chromosome of the cells. It can also be present in the cells in one or more copies. If the cells each contain more than one copy, these copies can be carried by one or more vectors, or by the chromosome. In every case, the exogenous sequence introduced into the cells of the FreeStyle™ 293-F encodes a functional protein, that is to say that the biological activity of the protein is preserved.

In the context of this invention, the terms and expressions "function" or "biological function" or "activity" or "biological activity" are equivalent. Similarly, the expressions "biologically active protein" or "active protein" or "functional protein" may hereinafter be used interchangeably.

The biological activity of the protein is "preserved" or "conserved" or "maintained" if it corresponds to that of the native protein. In other words, either the biological activity of the protein encoded by the exogenous nucleic acid sequence is identical to that of the native protein, or the difference between the two activities is insignificant.

The production of the protein is considered to be "stable" in the sense of this invention when it has a regular level, substantially constant over a period of at least 15 days, preferably at least one month, more preferably at least 1.5 months, or better yet, at least 2 months, at least 2.5 months or at least 3 months, or over even longer periods.

The production of the protein is "high level" when it yields at least 2 mg of protein per liter of culture medium, preferably at least 4 mg of protein per liter of culture medium, more preferably at least 6 mg of protein per liter of culture medium, and even more preferably at least 8 mg of protein per liter of culture medium, and, better yet, at least 10 mg of protein per liter of culture medium, and even more than that.

Since the FreeStyle™ 293-F cells are cultivated in suspension, it is easy for a person skilled in the art to increase the volume and/or the number of production units, in particular bioreactors. This is why the means of the present invention advantageously allow for large-scale production of the protein.

The qualitative and quantitative properties of the protein production (in particular the stability and yield) may possibly be dependent, in a more or less notable manner, on the conditions implemented. If necessary, a person skilled in the art can easily adapt, using simple routine tests, the conditions for implementing this invention, for example, based on the information reported in the examples below, depending on the protein to be produced.

It is of particular interest that the protein to be produced is of industrial, medical and/or research interest.

According to one embodiment, the protein is a mature protein. By "mature protein", it is referred here to a protein that may have been subjected to one or more posttranslational modifications. Among the posttranslational modifications, the following in particular can be cited: glycosylations, disulfide bonds, acetylations, amidations, biotinylations, carboxylations, hydroxylations, methylations, phosphorylations and sulfatations. The posttranslational modifications are well known to a person skilled in the art. In any case, the "mature" protein, in the sense of the invention, has a biological activity consistent with that expected (for example, according to the literature).

In the context of the invention, the protein of interest to be produced is the DKK1 protein. It is preferably the DKK1 protein of murine origin. According to the examples below, the DKK1 protein produced according to the invention can include additional sequences, such as V5 and/or 6H is tags, particularly useful for facilitating the detection and, if necessary, the purification of the protein. The recombinant cell line can advantageously be selected from lines 1B9 and 3F8 (cited in the examples below) respectively deposited at the CNCM (Collection Nationale de Cultures de Microorganismes, Institut Pasteur, 25 rue du Docteur Roux, 75724 Paris Cedex 15, France) on Apr. 7, 2005 under numbers I-3472 and I-3473. A preferred recombinant cell line is line 3F8 deposited at the CNCM on Apr. 7, 2005 under number I-3473.

A second aspect of this invention relates to a recombinant cell line as described above. Such a cell line is derived from the FreeStyle™ 293-F mammalian cell line and is capable of producing, stably and with high level, biologically active DKK1 protein.

More specifically, the recombinant cell line according to this invention is selected from lines 1B9 and 3F8 respectively deposited at the CNCM on Apr. 7, 2005 under numbers I-3472 and I-3473. A preferred recombinant cell line is line 3F8 deposited at the CNCM on Apr. 7, 2005 under number I-3473.

This invention also relates to the expression vectors of DKK1 protein, which, if necessary, will be contained in the cells of the recombinant'line derived from the FreeStyle™ 293-F cells. An example of a vector for expression of the DKK1 protein of murine origin is the vector pSK-GW-032 described in the examples below. This vector is contained in recombinant cell lines 1B9 and 3F8 respectively deposited at the CNCM on Apr. 7, 2005 under numbers I-3472 and I-3473.

According to a third aspect, this invention relates to a method for the stable and high-level production of biologically active DKK1 protein, said method including at least:
a) the culture of a recombinant cell line as described above under appropriate conditions; and
b) the recovery of said protein.

The determination of the "appropriate culture conditions" is based on the general knowledge of a person skilled in the art, who may also refer to the suggestions of the manufacturer of the FreeStyle™ 293-F line.

According to one embodiment, the culture of step a) is preceded by at least:
i) the construction of a vector for expression of said protein;
ii) the transformation of the FreeStyle™ 293-F mammal cell line with the vector prepared in step i).

Steps i) and ii) use the general knowledge of a person skilled in the art who may, if he/she deems it useful, refer to the experimental procedures described in the examples below.

According to another embodiment, the culture of step a) is implemented in suspension. Cell suspension can be produced according to conventional methods, for example in Erlenmeyer, in Fernbach or in a bioreactor, in continuous or batch mode.

According to yet another embodiment, the culture of step a) is implemented in a medium free of animal serum. A person skilled in the art will advantageously select the FreeStyle™ 293-F Expression Medium commercial culture medium (Gibco, #12338-018).

According to yet another embodiment, the method according to the present invention also includes a step of purifying the protein, which purification does not alter, or it does not significantly alter, the biological activity of the protein. The purification can be performed using conventional methods such as purification on a nickel chelate affinity column, ion-exchange chromatography (anionic or cationic), heparin-sepharose column chromatography, and the like. Advantageously, the purification step thus implemented makes it possible to obtain a pure protein with at least about 80%, preferably at least about 85%, more preferably at least about 90%, still more preferably at least about 95%, and even more.

According to a preferred embodiment, the method of this invention is implemented on a large scale. By "large scale", it is referred here to a high production capacity using large volume and/or a large number of production units. Purely by way of indication, it can be considered that the production is on a large scale when, for example, at least 100 liters of culture supernatant are prepared (if a plurality of reactors are used, the culture volume in each of them can be reduced proportionally while still remaining at a "large scale" level of production).

The following figures are intended to illustrate, in relation to the examples below, specific embodiments of this invention:

FIG. 1A: effect of heparin addition to the culture medium on the amount of DKK1-V5-6H is collected (semi-quantitative "Dot Blot"). A, B and C correspond to the deposits of 100 μl of culture supernatants of the 3 different clones expressing DKK1-V5-6H is.

FIG. 1B: analysis of the expression in different cellular clones ("Dot Blot")

FIG. 1C: analysis of the expression on concentrated culture media
SDS-PAGE 10 to 20% with Coomassie blue stain
Lanes 1 to 3: BSA (0.2; 1 and 2 μg)
Lanes 4 to 6: parental cells 293-F, culture supernatant concentrated 12.5 times (5, 10, 20 μl)
Lane 7: Seeblue MW (5 μl)
Lanes 8 to 10: clone 3F8, culture supernatant concentrated 12.5 times (5, 10, 20 μl)

FIG. 1D: clarification of raw extracts by filtration SDS-PAGE 10 to 20% with Coomassie blue stain
1: raw material
2: filtration on membrane of 0.8 μm (Millex AA MCE membrane)
3: filtration on membrane of 0.45 μm (Millex AV PVDF membrane)
4: filtration on membrane of 0.2 μm (Millex AV PVDF membrane)
5: two successive filtrations on membrane of 0.2 μm (Millex GV Durapore membrane).

FIG. 1E: clarification of the raw extracts by centrifugation
A: cell culture supernatants
B: A clarified by centrifugation at 16000×g for 3 h
C: B+buffer containing 20 mM of imidazole
D: centrifugation pellet (concentrated 10 times)
E: passage through a nickel column
MW. Molecular weight standard FIG. 2A: Analysis of the purity of the protein purified on elution fractions of the nickel chelate column
SDS-PAGE 10 to 20% with Coomassie blue stain
MW. Molecular weight standard
Load: 4 μl of each fraction FIG. 2B: analysis of the inhibitory action of DKK1-V5-6H is on the Wnt transduction metabolic pathway
Dosage effect of DKK1 on L21+/−Wnt3a
Protein DKK1-V5-6His: lot 1029-123P (conservation at 4° C. for 5 days before the test). Concentration estimated at 0.5 mg/ml. Dilution of the protein in Opti DMEM medium. DKK1 protein concentration expressed in final ng/ml.

Test specimen: cells not treated with Wnt but exposed to various amounts of DKK1.

Control: cells treated with Wnt without DKK1

Figure 3:
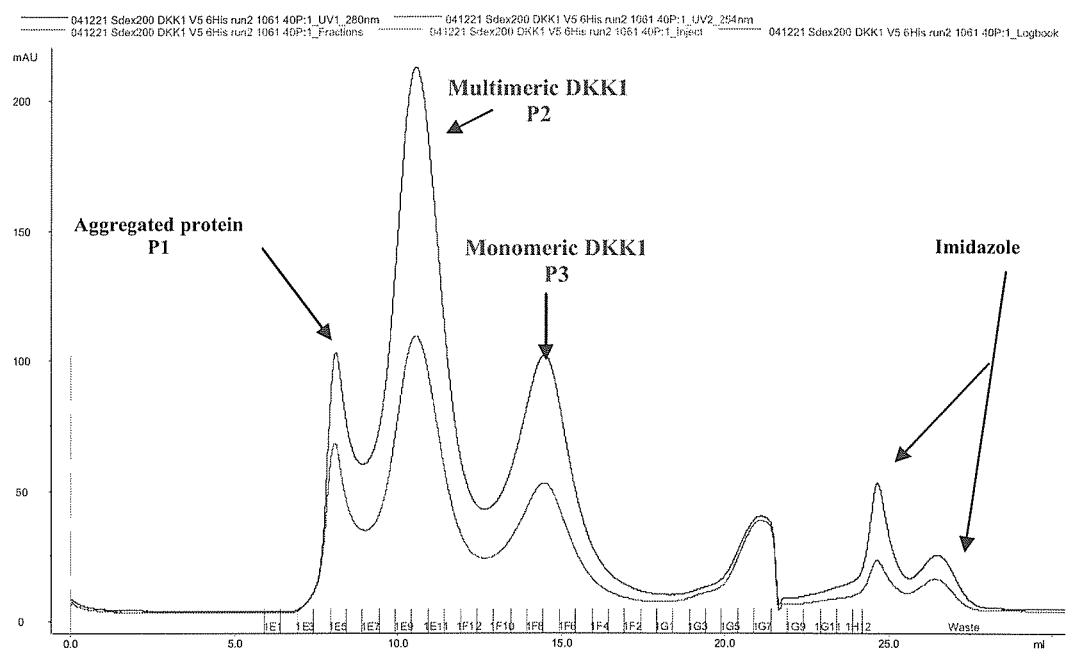
Figure 3:
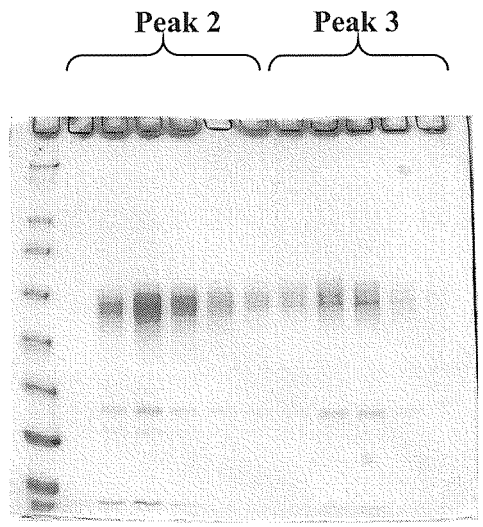
Figure 3:
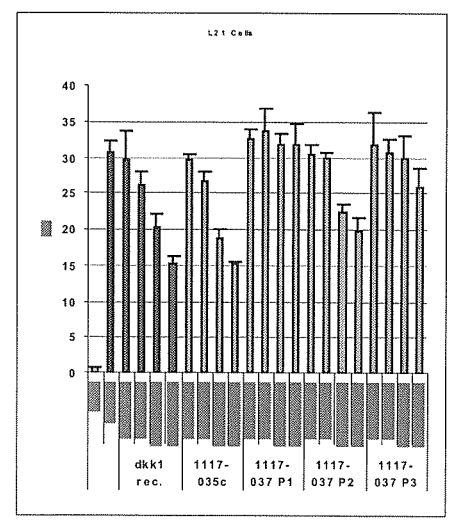

FIG. 3A: analysis of the oligomerisation state of DKK1 by exclusion chromatography on Superdex 200 HR 10-30 column (24 M1)

Buffer: PBS. Injection: 250 µl of lot 1061-40P. Flow rate 0.4 ml/min

P1: peak1; P2: peak2; P3: peak3

FIG. 3B: SDS-PAGE/Coomassie blue on the fractions

Load: 20 µl of each fraction

FIG. 3C: specific activity on the Wnt pathway

Figure 4:
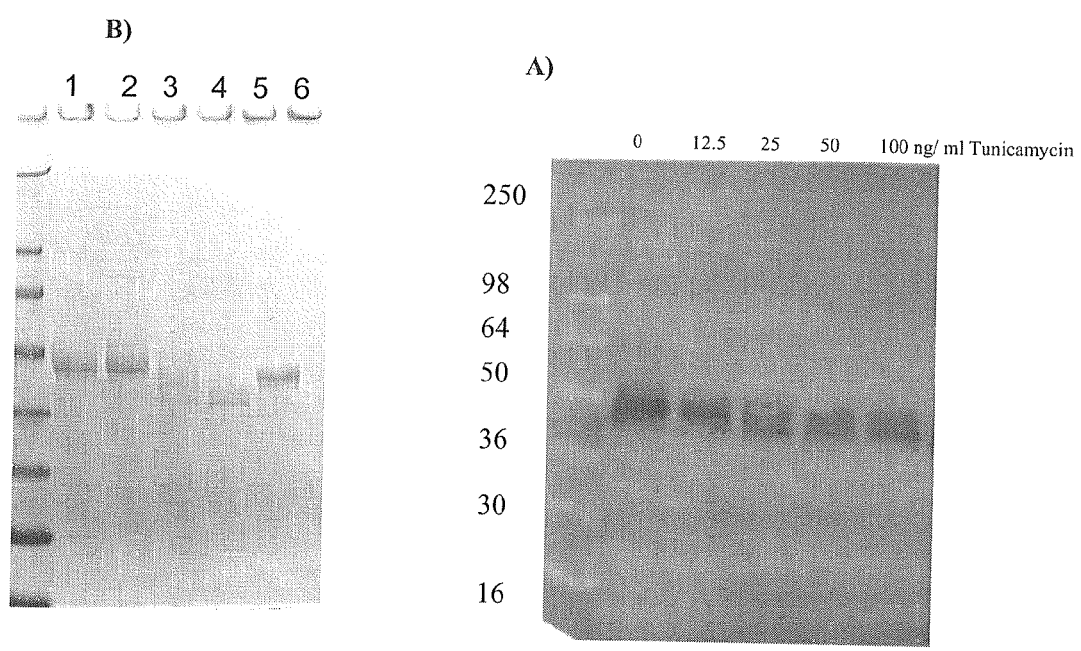

FIG. 4A: analysis by Western Blotting of the effect of a treatment of 3F8 cells with tunicamycin on the electrophoretic migration of the DKK1-V5-6H is protein Load: 16 µl of culture supernatant of the 3F8 clone cultivated for 24 h in the presence of the indicated quantity of tunicamycin.

FIG. 4B:
Study of native deglycosylation
1: no treatment
2: incubation at 37° C. without deglycosylation enzyme
3: incubation with PNGase
4: incubation with PNGase and neuraminidase
5: incubation with neuraminidase Other aspects, embodiments and advantages may become clear from the following examples, intended as non-limiting illustrations of the subject matter of the present invention.

SUMMARY OF THE EXPERIMENTAL EXAMPLES

Murine DKK1 sequence was cloned upstream the IgK signal peptide sequence for secretion by mammalian cells and fused to V5 and 6H is tags for detection and purification. Expression was placed under the control of the pEF-1alpha constitutive promoter. This construct was transfected into five different mammalian cell lines in order to produce the recombinant protein in the culture medium. Stably transfected clones were obtained for all of these lines and the highest levels of expression were observed in clones obtained with the commercially available FreeStyle™ 293-F cell line. These cells can be cultivated in suspension, which allows for easy scaling-up of production in bioreactor (by batch or by perfusion). Their commercial culture medium is free of animal serum, thus eliminating potential contamination problems and allowing for easy purification of the protein by a one-step procedure. A high production level can be maintained over time without difficulty, in particular for at least 2 months. The DKK1 protein thus produced was mature, that is to say that it was posttranslationally modified and highly active in biological assays.

I—Experimental Procedures

I-1—Reagents:

Trizma hydrochloride (Sigma # T-3253), trizma base (Sigma # T-1503), NaCl (Fluka #71376), ethylene-diamine tetra-acetic acid (EDTA, Sigma # E-5391), imidazole (Fluka #56750), nickel sulfate hexahydrate (Fluka #72280).

I-2—Vectors pSK-GW-032 Vector

The mouse Dkk1 sequence lacking the putative signal peptide (of aa31 to the end) was amplified from a cDNA library using primers containing the HindIII and EcoRI restriction sites. The PCR product was first cloned into the HindIII/EcoRI-digested pSecTag-2C plasmid (Invitrogen). The resulting Igk-Dkk1 (aa3'-end) in-frame sequence was then amplified using primers designed to allow for recombination into the gateway entry plasmid pDONR201 (Invitrogen). The sequence Igk-Dkk1 (aa31-end) was finally cloned by recombination into the gateway acceptor mammalian expression plasmid pEF-Dest 51 (Invitrogen).

I-3—Cell Culture

All cells used in these studies were commercially available mammalian cell lines: HEK-293 (ATCC CRL-1573), BHK-21 (ATCC CCL-10), CHO (ATCC CCL-61), L cells (RIKEN cell bank) and FreeStyle™ 293-F cells (Invitrogen # R790-07).

L cells were grown in DMEM (Gibco #31053-028), CHO cells in DMEM (Gibco #31053-028)/F12 (HAM) (Gibco #21765-029), BHK cells in DMEM/F12 (without phenol red) (Gibco #21041-025) and HEK-293 cells in DMEM with glucose at 4.5 g/liter (Gibco #041-01966).

The following were added to all of these media: 5% FBS (Sigma # F2442), 1% sodium pyruvate (BioWhittaker # BE13-115E), 1% L-glutamine (BioWittaker # BE17-605E), 100 U/ml of penicillin and 100 µg/ml of streptomycin (Bio-Whittaker # DE17-602E).

The FreeStyle™ 293-F cells were grown in a FreeStyle 293 Expression Medium (Gibco #12338-018) containing 100 U/ml of penicillin and 100 µg/ml of streptomycin.

Blasticidin at 0.5 µg/ml (Invitrogen #R210-01) was added in order to select stably transfected cells. Heparin (Sigma # H3149) was added at 0.1 g/liter for production.

I-4—Obtention of Stably Expressing Cells

Various commercially available mammalian cell lines (HEK-293, BHK-21, CHO, L-cells and FreeStyle™ 293-F cells) were transfected with the pSK-GW-032 vector. Stably expressing clones were obtained for each cell line after selection with 10 µg/ml of blasticidin (Invitrogen; # R210-01). After selection with blasticidin, a sub-cloning was performed in 96-well plates by dilution of the cells, and the DKK1 protein expression was tested for all clones by "Dot blot" analysis.

I-5—Scaling-Up for Production—Perfusion Test

For production scaling-up, the 3F8 clone (CNCM I-3473) was selected.

The production was successfully tested using 3 different approaches: plastic Erlenmeyer with agitation in 8% $CO_2$ incubator (INFORS), CellSpin production bottle (Integra Biosciences) in an incubator under 8% $CO_2$ and bioreactor, either in the batch mode or in perfusion mode.

I-6—"Blots"

For the Western blot, electrophoresis was performed according to the SDS-PAGE method. Proteins were then transferred from the gel to a PVDF membrane (Biorad) by applying a 45 mA constant current overnight to a transfer cell (Invitrogen X cell II) in Tris-glycine transfer buffer (Invitrogen # LC 3675).

For the "Dot blots", nitrocellulose filters (Hybond ECL, Amersham # RPN 303D, 11 cm×7.5 cm) were incubated with PBS before loading of 100 µl of conditioned medium per well, then each well was washed 3 times with 200 µl of PBS.

In both cases, saturation of the filters was 1 hour at room temperature in PBS containing 5% skim milk (Difco #232100) and 0.5% Tween 20 (Fluka #93773), followed by an overnight incubation at 4° C. with the primary antibody (anti-tetra-His (Qiagen #34670) at 0.05 µg/ml final) in the same buffer. After 3 washes for 15 min in PBS 1X+0.2% Tween 20+0.35 M NaCl, the filters were then incubated with the secondary antibody (sheep anti-mouse IgG (Amersham # NA931V), dil. 1/2000) for 1 hour in PBS 1X+5% skim milk+ 0.5% Tween 20 at room temperature. After 3 washes for 15 min in PBS 1X+0.2% Tween 20+0.35 M NaCl, the "dots"

were then revealed using ECL+solution (Amersham # RPN 2132) and a Fx phosphorimager.

I-7—Purification of the Protein

The conditioned medium (CM) was centrifuged at 500×g for 10 min so as to remove the cell debris, then stored at −20° C. until use. After thawing, the 10× buffer was added to the CM so as to obtain 50 mM Tris, pH 8.0, 100 mM NaCl and 20 mM imidazole in final concentrations. Clarification of the solution was achieved either by membrane filtration on 0.22 μm GP Express PLUS membrane (Millipore # SCGPU02RE) or Centrifugation at 8000×g for 3 hours 30 min at 4° C. The clarified medium was then loaded at 5 ml/min (i.e., 56.6 cm/h) onto a 50-ml affinity column (Chelating Sepharose Fast Flow resin (Amersham #17-0575-02) first loaded with 0.5 M nickel sulfate hexahydrate solution, then equilibrated in buffer A (50 mM Tris, pH 8.0, 250 mM NaCl and 20 mM imidazole). After extensive wash in buffer A, elution was conducted using imidazole gradient to 250 mM.

I-8—Characterisation of the Protein

The conventional technique (SDS-PAGE with Coomassie blue stain) was used. Deglycosylation experiments were conducted on the purified protein using N-glycosydase (Roche #1365169) or Neuraminidase (SIGMA # N8271) under the conditions recommended by the suppliers. The existence of a glycosylation-type posttranslation modification was also identified directly in vivo by treating cells with different concentrations of tunicamycin (SIGMA # T7765) for 24 hours. The oligomerisation state of DKK1-V5-6His was analysed by separation on exclusion chromatography using a Superdex HR 10-30 column (Amersham BioScience #17-108801) equilibrated under PBS.

I-9—Cellular DKK1 Protein Activity Assay

Cells were plated in 24-well dishes at $2\times10^4$ cells/cm$^2$ 24 hours prior transfection, then they were transiently transfected with the indicated constructs (1 μg of DNA total) using the Fugene 6 DNA-lipid complex (Boehringer Manheim) according to the manufacturer's protocol. Sixteen hours after transfection, cells were washed, and cultured in a medium containing 2% fetal calf serum for an additional 48 hours under the conditions indicated. Cells were then assessed for luciferase activities. The TCF1 expressing constructs (300 ng/well) were transfected together with the TOPFLASH-luciferase (200 ng/well). To assess transfection efficacy, 20 ng of pRL-TK (Promega) encoding a Renilla luciferase gene downstream of a minimal HSV-TK promoter was systematically added to the transfection mix, Luciferase assays were then performed with the Dual Luciferase Assay Kit (Promega) according to the manufacturer's instructions. 10 μl of cell lysate was assayed for firefly luciferase activity, then for Renilla luciferase activity. Firefly luciferase activity was normalized to the Renilla luciferase activity.

To test the activity of recombinant DKK1 protein, transfected cells were treated with the indicated concentration in the presence of Wnt3a conditioned medium. Wnt3a conditioned medium (Wnt3a-CM) was prepared from L cells producing Wnt-3a as described by Shibamoto et al. (Shibamoto, 1998). Controls were carried out with Wnt3a in the absence of recombinant DKK1 protein or with cells in the absence of both Wnt3a-CM and recombinant DKK1 proteins.

II—Results

II-1—Obtention of Stably Expressing Cells and Protein Production

Various mammalian cell lines available on the market (cells HEK-293, BHK-21, CHO and L cells) were transfected with pSK-GW-032 vector. Stably expressing clones were obtained for each cell line after selection with 10 μg/ml of blasticidin. Table 1 below shows the results for the most interesting expression clones.

TABLEAU 1

|  |  | Frozen isolated clones | Positive clones | Highest expression levels |
|---|---|---|---|---|
| Adherent cells | HEK | 15 | 3 | 0.25 mg/litre |
|  | BHK | 19 | 12 | 0.25 mg/litre |
|  | CHO | 29 | 6 | 0.05 mg/litre |
|  | L cells | 38 | 20 | 2 mg/litre |
| Non-adherent cells | 293 F cells |  |  | 10 mg/litre |

To estimate the expression level for each clone, a semi-quantitative "Dot Blot" analysis was performed with the GST-6His-RANK protein as a control for well defined amounts of protein, and revelation was made using the widely used anti-tetra-His antibody (Qiagen). When culture medium was supplemented with heparin at 0.1 g/liter, the rate of recovery of DKK1 protein in the culture medium was increased by a factor 10 (FIG. 1A). The expression levels obtained for these clones were similar to those usually obtained for mammalian cells, between 0.1 and 2 mg of protein of interest per liter of conditioned medium, depending on the cell line and the clone analysed (FIG. 1B, table 1).

These expression levels were not satisfying insofar as the objective was to produce more than 100 mg of protein. In addition, these cells were adherent cells, which cannot easily be used for production scaling up. The DKK1 protein was then expressed in a quite new commercially available cell line growing in suspension: FreeStyle™ 293-F cells. This cell line was only described for transient transfection experiments. Transfection was performed as described by the manufacturer. After selection under blasticidin, a sub-cloning was performed in 96-well plates by cell dilution. Expression was tested for all resistant clones by "Dot Blot" analysis. Six clones were found to be highly positive and were amplified. The expression level of the two best clones (1B9 [CNCM I-3472] and 3F8 [CNCM I-3473]) was tested by SDS-PAGE/Coomassie blue stain and estimated between 4 and 10 mg of DKK1 protein/liter of conditioned medium, depending on the culture conditions (FIG. 1C).

Scaling up of the production was performed using different culture approaches [CellSpin (12 liters), regulated bioreactors either in batch mode (10 liters), or in perfusion mode (50 liters)] with similar expression levels. Cells were shown to be very strong (good viability during the perfusion experiment) and expression was constant for at least 2 months (data not shown).

II-2—Purification of the Protein

The carboxy-terminal 6H is tag was used to purify the protein. Cell supernatants were collected by low speed centrifugation and buffered by adding 50 mM This at pH 8.0. To reduce the non-specific binding of contaminant proteins on the nickel chelate column, 20 mM of imidazole and 150 mM of NaCl were added to this solution. A second clarification was performed to remove any insoluble material by high-speed centrifugation or by filtration. Non-specific binding occurred when a membrane of 0.8 μm Millex AA MCE was used. The protein was not adsorbed either on a membrane of 0.2 μm Millex GV Durapore or a membrane of 0.22 μm GP Express PLUS (FIG. 1D). During loading, a low but constant leaching of the nickel out of the resin was observed. This limited the total amount of medium that could be loaded onto the column without loss of the DKK1-V5-6His protein in the flowthrough, to 120 volumes of column (in this case, 6 liters used for the 50-ml column). Under these conditions, the protein always eluted between 90 and 100 mM of imidazole.

II-3—Characterisation of the Protein

Figure 2:
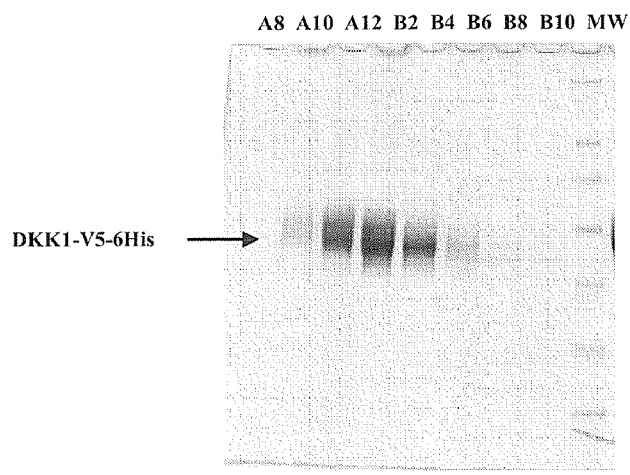
Figure 2:
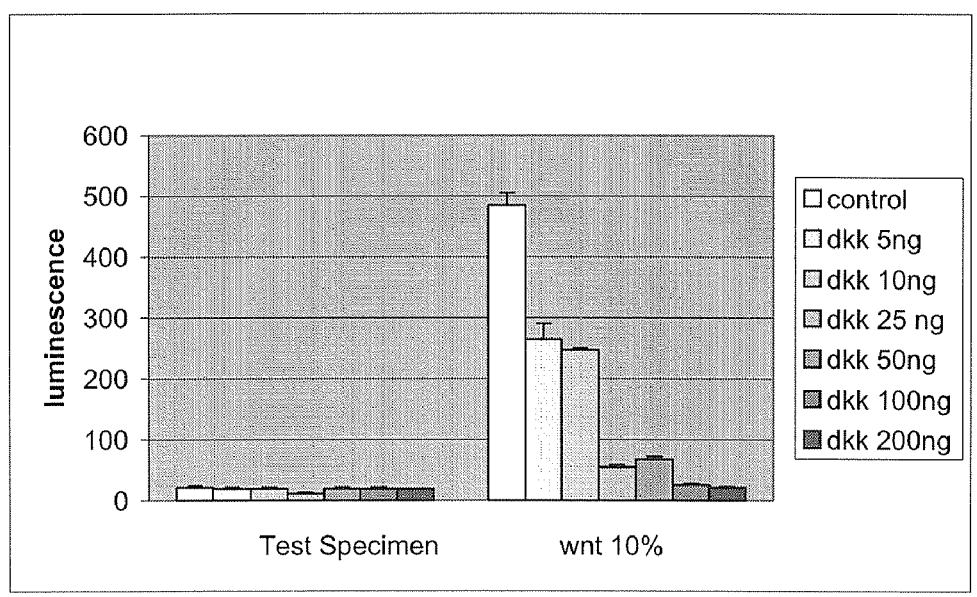

The protein was about 90% pure after the nickel chelate purification step as shown by the SDS-PAGE analysis with Coomassie blue stain (FIG. 2A). As already described in the literature, the DKK1 protein migrated as a diffuse multiband pattern, characteristic of glycosylated proteins.

All of the protein batches tested were biologically active, as shown by good dose-response dependent activities in a cell assay for inhibition of the Wnt transduction pathway (FIG. 2B). When the protein was analysed using an exclusion chromatography column (Superdex 200 resin), 3 distinct peaks were observed by UV (280 nm) with retention times compatible with aggregates, high molecular weight complexes and monomeric form (FIG. 3A). This result was confirmed with a plurality of different preparations. The SDS-PAGE analysis with Coomassie blue stain showed that most of the protein was eluted with a retention time corresponding to that of multimers and monomers (FIG. 3B). A slight difference could be noted in the composition of the bands between these two peaks. The multimer and monomer forms of the proteins were tested for Wnt pathway inhibition. They had the same activity (FIG. 3C).

The protein was well glycosylated, as shown by a clear shift in the migration on SDS-PAGE of the protein obtained from 3F8 cells treated with tunicamicyn, a glycosylation inhibitor (FIG. 4A). Cell viability (76%) and cell concentration ($4.45 \times 10^5$ cells/ml) were reduced with respect to those of untreated cells (88%, $8 \times 10^5$ cells/ml) for the treatment at the highest dose (100 ng/ml). The type of glycosylation was studied using the purified protein. PNGase treatment induced a shift in all of the discrete bands shown by SDS-PAGE/Coomassie blue, clearly showing the presence of N-glycosylation (FIG. 4B). Nevertheless, the pattern was still multiband, indicating that the protein remained heterogeneous. A shift of the protein was also observed when it was incubated with Neuraminidase alone, showing the presence of sialic acids at the end of the carbohydrate chain. Co-treatment with PNGase and Neuraminidase led to a higher shift in the bands, but the aspect remained heterogeneous and there was no difference after longer treatments (FIG. 4B). It appeared that the sialic acids were eliminated even after the action of the PNGase, showing that the enzyme was partially active or that there were more than one sites of glycosylation in the protein.

The treatment with O-glycosydase did not cause any shift in the protein.

REFERENCES

Peifer and Polakis 2000. Science 287: 1606-1609
Glinka et al, 1998. Nature 391: 357-362
Grotewold et al, 1999. Mech. Dev. 89: 151-153
Fedi et al, 1999. J. Biol. Chem. 274: 19465-19472
Krupnik et al, 1999. Gene 238: 301-313
Shibamoto et al, 1998. Genes to Cells 3: 659-670

The invention claimed is:

1. Recombinant cell line derived from the 293-F mammalian cell line and selected from among lines 1B9 and 3F8, respectively deposited at the CNCM (Collection Nationale de Cultures de Microorganismes, Institut Pasteur, 25 rue du Docteur Roux, 75724 Paris Cedex 15, France) on Apr. 7, 2005 under no 1-3472 and 1-3473.

* * * * *